(12) United States Patent
Caruel et al.

(10) Patent No.: US 9,706,770 B2
(45) Date of Patent: Jul. 18, 2017

(54) RODENTICIDE BAIT COMPRISING DIFENACOUM AND METHOD FOR CONTROLLING TARGET RODENT PESTS

(71) Applicants: LIPHATECH, Pont-du-Casse (FR); VETAGRO SUP, Marcy l'Etoile (FR)

(72) Inventors: Herve Caruel, Moncaut (FR); Bernadette Espana, Marcy L'Etoile (FR); Stephane Besse, Francheville (FR); Virginie Lattard, Lyons (FR); Etienne Benoit, Lyons (FR)

(73) Assignees: LIPHATECH, Pont-du-Casse (FR); VETAGRO SUP, Marcy l'Etoile (FR)

( * ) Notice: Subject to any disclaimer, the term of this patent is extended or adjusted under 35 U.S.C. 154(b) by 0 days.

(21) Appl. No.: 15/318,195

(22) PCT Filed: Jun. 11, 2015

(86) PCT No.: PCT/EP2015/063026
§ 371 (c)(1),
(2) Date: Dec. 21, 2016

(87) PCT Pub. No.: WO2015/189319
PCT Pub. Date: Dec. 17, 2015

(65) Prior Publication Data
US 2017/0105408 A1    Apr. 20, 2017

(30) Foreign Application Priority Data

Jun. 13, 2014 (FR) .................................... 14 55437

(51) Int. Cl.
| | | |
|---|---|---|
| *A01N 43/16* | (2006.01) |
| *C07D 311/56* | (2006.01) |
| *A01N 25/00* | (2006.01) |
| *A23K 50/50* | (2016.01) |
| *A23K 10/30* | (2016.01) |

(52) U.S. Cl.
CPC .......... *A01N 25/004* (2013.01); *A01N 43/16* (2013.01); *A23K 10/30* (2016.05); *A23K 50/50* (2016.05)

(58) Field of Classification Search
None
See application file for complete search history.

(56) References Cited

FOREIGN PATENT DOCUMENTS

| EP | 0 147 052 A2 | 7/1985 |
| EP | 2 090 164 A1 | 8/2009 |
| WO | 93/01712 A1 | 2/1993 |

OTHER PUBLICATIONS

Winn, M.J., et al: "An investigation of sex-linked differences to the toxic and to the pharmacological actions of difenacoum: studies in mice and rats", Journal of Pharmacy and Pharmacology, vol. 39, No. 3, Mar. 1, 1987 (Mar. 1, 1987), pp. 219-222, XP055148402, ISSN: 0022-3573, DOI: 10.1111/j.2042-7158.1987.tb06252.x.
International Search Report, dated Aug. 21, 2015, from corresponding PCT Application.

*Primary Examiner* — Robert A Wax
*Assistant Examiner* — Randeep Singh
(74) *Attorney, Agent, or Firm* — Young & Thompson

(57) ABSTRACT

Disclosed is a rodenticide bait including: difenacoum in the form of trans-difenacoum of formula 3-(biphenyl-4-yl)-1-(4-hydroxycoumarin-3-yl)-1,2,3,4-tetrahydronaphthalene, in wherein carbons 1 and 3 of group 1,2,3,4-tetrahydronaphthalene of the trans-difenacoum have the same absolute configuration; and an edible excipient for target rodent pests. The bait includes trans-difenacoum at a concentration above a minimum trans-difenacoum concentration lethal to female adults of the target rodents, but below a minimum trans-difenacoum concentration lethal to adult males of the target rodents, the minimum concentration lethal to female adults being less than the minimum concentration lethal to male adults. Also disclosed is a method for selectively controlling a population of target rodent pests.

17 Claims, 4 Drawing Sheets

RODENTICIDE BAIT COMPRISING DIFENACOUM AND METHOD FOR CONTROLLING TARGET RODENT PESTS

The invention relates to a rodenticidal bait comprising difenacoum and a method of combating target rodent pests. The invention therefore relates to the technical field of combating excessive development of populations of target rodent pests.

It is known to use traps for target rodent pests allowing the removal of a small number of individuals of a species of target rodent pest. Rodenticidal baits serving as poison for target rodent pests are also known.

Rodenticidal baits and methods for combating rodent pests are already known. Such a rodenticidal bait comprises, for example, difenacoum in a proportion by mass of 50 mg per kilogram (0.005%, 50 ppm) of bait. In particular, WO 93/01712 describes rodenticidal baits comprising difenacoum in an amount of 0.0025% or 0.005% (by weight) in the form of granules known by the name "Klerat pellets" and packaged in a paper sachet and impregnated with denatonium benzoate as a bittering agent.

Such baits pose problems when they are made available to populations of rodent pests, and in spite of their composition conferring on them a bitter taste, they are liable to be eaten by animals other than the rodent pests. For example, they may be eaten by domestic animals and pets. They may also be accidentally eaten by humans.

In addition, a significant amount of difenacoum in these known rodenticidal baits may be ingested by predators—in particular birds—or carrion eaters of rodent pests and in particular rodent pests weakened by having eaten such a rodenticidal bait, this eating being liable to cause in the end the death of these animal predators or carrion eaters.

The object of the invention is therefore to compensate these disadvantages by proposing a rodenticidal bait and a method of combating target rodent pests which are effective for controlling populations of rodent pests and which nevertheless allow limiting of the risks of poisoning of humans and non-target animals.

The object of the invention in particular is such a rodenticidal bait and such a method of combating target rodent pests which allow limiting of the risks of poisoning of animal predators, such as, for example, domestic or wild mammals—in particular foxes—and bird predators or carrion eaters of rodent pests.

The object of the invention is also such a rodenticidal bait and such a method of combating target rodent pests the implementation of which complies with the rules of good usage in particular with respect to protection of birds, and in particular birds of prey.

The object of the invention is also such a rodenticidal bait and such a method of combating target rodent pests which allows limiting of the risks of poisoning of domestic animals and pets.

The object of the invention is also in particular a method of combating target rodent pests which does not require the use of massive doses of rodenticidal agents and which is respectful of the environment, the health of humans and non-target animals.

To this end, the invention relates to a rodenticidal bait comprising
  difenacoum in the form of trans-difenacoum of formula 3-(biphenyl-4-yl)-1-(4-hydroxycoumarin-3-yl)-1,2,3,4-tetrahydronaphthalene, in which carbon atoms 1 and 3 of the 1,2,3,4-tetrahydronaphthalene grouping have the same absolute configuration, and
  an excipient which is edible for target rodent pests;
characterised in that it comprises a proportion of trans-difenacoum in the bait which is greater than a minimum proportion of trans-difenacoum which is lethal to adult females of the target rodents and less than a minimum proportion of trans-difenacoum which is lethal to adult males of the target rodents, said minimum proportion which is lethal to adult females being less than the minimum proportion which is lethal to adult males.

The invention thus relates to a bait that is rodenticidal towards a population of target rodent pests and comprising trans-difenacoum, in which the proportion of trans-difenacoum in the bait is greater than a minimum proportion of trans-difenacoum which is lethal to adult females of the target rodents and less than a minimum proportion of trans-difenacoum which is lethal to adult males of the target rodents, said minimum proportion which is lethal to adult females being less than the minimum proportion which is lethal to adult males.

The invention thus relates to such a rodenticidal bait comprising difenacoum in the form of a configurational stereoisomer of difenacoum, called trans-difenacoum, said trans-difenacoum having the formula 3-(biphenyl-4-yl)-1-(4-hydroxycoumarin-3-yl)-1,2,3,4-tetrahydronaphthalene, carbon atoms 1 and 3 of the 1,2,3,4-tetrahydronaphthalene grouping of trans-difenacoum having the same absolute configuration, and an excipient which is edible for target rodent pests.

Throughout the text:
  the general term "difenacoum" denotes 3-(biphenyl-4-yl)-1-(4-hydroxycoumarin-3-yl)-1,2,3,4-tetrahydronaphthalene or 3-(biphenyl-4-yl-1,2,3,4-tetrahydro-1-naphthyl)-4-hydroxycoumarin, also called 2-hydroxy-3-[3-(4-phenylphenyl)-1-tetralinyl]-4-chromenone in IUPAC ("*International Union of Pure and Applied Chemistry*") nomenclature. trans-Difenacoum has the structural formula (I) shown below:

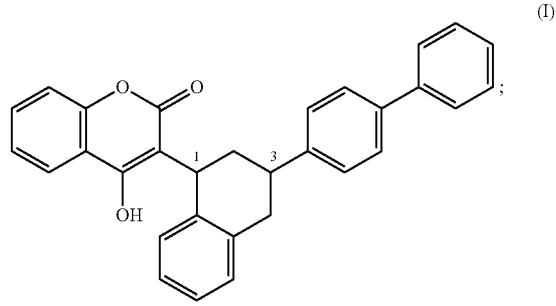 [SMILES: O=c1oc2ccccc2c(O)c1C1CC(c2ccc(-c3ccccc3)cc2)Cc2ccccc21]

in which carbon atoms "1" and "3" of the 1,2,3,4-tetrahydronaphthalene grouping are identified. In trans-difenacoum, the substituent (4-hydroxycoumarin-3-yl) of carbon atom 1 on the one hand and the substituent (biphenyl-4-yl) of carbon atom 3 on the other hand extend in the "trans" direction with respect to the median plane of the atoms of the 1,2,3,4-tetrahydronaphthalene grouping and carbon atoms 1 and 3 of the 1,2,3,4-tetrahydronaphthalene grouping have the same absolute configuration;
  "stereoisomers" designates isomers of difenacoum of the same semi-structural formula, but in which the relative position of the atoms differs spatially. "Configurational stereoisomers" designates stereoisomers of which the conversion from one to the other of the stereoisomers requires a rupture/reformation of an interatomic covalent bond. Thus, "configurational stereoisomers" denotes stereoisomers which are not conformational isomers (or "rotamers", of which the conversion from one to the other of the conformational isomers is accompanied solely by a rotation of a part of the molecule around the axis of a σ bond formed by axial overlapping of orbitals). The same configurational stereoisomer may be formed from one to the other of the possible different enantiomers of this configurational stereoisomer or from a racemic or non-racemic mixture of these possible enantiomers;

the absolute configurations of carbon atoms 1 and 3 of the 1,2,3,4-tetrahydronaphthalene grouping are determined by the Cahn, Ingold and Prelog nomenclature;

the expression "minimum lethal proportion" of trans-difenacoum in a bait means the lowest proportion—especially the mass proportion—of trans-difenacoum in said bait that is capable of killing at least one individual of the population of target rodent pests by eating of said bait. The minimum lethal mass proportion of trans-difenacoum of a bait is thus the proportion (in grams of trans-difenacoum per gram of bait) that can kill at least one individual of the population of target rodent pests by eating of said bait by this individual of the population of target rodent pests.

The minimum proportion of trans-difenacoum which is lethal to adult females the population of target rodents is determined by measuring the mortality rate for adult females in batches of target rodent pests which eat baits over a predetermined period, the baits being provided to each of the batches in an amount sufficient to satisfy the appetite of the target rodents and comprising a predetermined proportion of trans-difenacoum. The minimum proportion of trans-difenacoum which is lethal to adult females is the proportion of trans-difenacoum of the baits which is made available to and ingested by the batch of target rodents and which has the lowest non-zero mortality rate by haemorrhage in females.

Similarly, the proportion of trans-difenacoum which is lethal to adult males of the population of target rodents is determined by measuring the mortality rate for adult males in batches of target rodent pests eating the baits over a predetermined period, the baits being made available to each of the batches in an amount sufficient to satisfy the appetite of the adult males of the target rodents and comprising a predetermined proportion of trans-difenacoum. The proportion of trans-difenacoum is termed non-lethal to the adult males if the baits provided to the batch of target rodents do not cause any death by haemorrhage in the target adult male rodents.

Advantageously and according to the invention, the excipient which is edible comprises at least one food chosen from the group formed by cereal grains—in particular shelled cereal grains-, ground cereal grains, cereal grain flours, cereal grain flakes, cereal bran, non-cereal grains—for example alfalfa grains-, ground non-cereal grains, non-cereal grain flours, non-cereal grain flakes, and non-cereal plant bran. The excipient which is edible can comprise any food which is liable to be eaten by the target rodent pests.

Advantageously and according to the invention, the excipient which is edible is chosen so as to be able to be eaten by target rodent pests. The invention thus relates to a rodenticidal bait which comprises a composition comprising trans-difenacoum in a majority in difenacoum and an excipient which is edible that is capable of stimulating target rodent pests to eat said bait.

Advantageously and according to the invention, the excipient which is edible is non-lethal to target rodent pests.

In particular, the excipient which is edible is not rodenticidal per se and is free of rodenticidal compounds. Advantageously and according to the invention, the excipient which is edible is chosen to stimulate the eating of the bait by target rodent pests and to allow eating of the bait by target rodent pests.

Advantageously, the excipient which is edible comprises at least one food chosen from the group formed by foods of vegetable origin and foods of animal origin. Advantageously, the food is chosen from the group formed by grains of one or more cereals, shelled grains of one or more cereals, one or more ground cereals, flakes of one or more cereals, bran of one or more cereals and flours of one or more cereals. By way of example, the food is chosen from the group formed by oat, wheat, barley, maize, soya and rice.

Advantageously, the excipient which is edible comprises at least one sugary food. For example, it may be a food comprising at least one sugar chosen from the group formed by sucrose, lactose, fructose and glucose. It may be a sugar syrup—for example a sugar syrup obtained by hydrolysis of starch—or a sugar syrup obtained by hydrolysis of sucrose (invert sugar syrup), or a beetroot sugar syrup, or a maple syrup, or a sugar cane syrup, or a syrup obtained from a plant of the *Stevia* genus.

Advantageously, the excipient which is edible comprises at least one food for stimulation of the appetite of the target rodent pests chosen from the group formed by flakes and flour of coconut kernel albumen (copra).

Advantageously, the excipient which is edible comprises at least one food for stimulation of the appetite of the target rodent pests chosen from the group formed by walnuts, hazelnuts and almonds—grated and/or in powder form.

Advantageously, the excipient which is edible comprises at least one fatty substance chosen from the group formed by vegetable fats, vegetable oils (for example rapeseed oil, soya fat, sunflower oil, cacao butter, peanut oil, peanut butter, maize oil, palm oil), animal fats and animal oils (butter, lard, fish oil).

Advantageously, the excipient which is edible comprises at least one food chosen from the group formed by animal proteins. By way of example there may be mentioned, for example, powdered milk—in particular skimmed milk powder—eggs—in particular powdered eggs—and hydrolysates of animal proteins.

Advantageously and according to the invention, the rodenticidal bait is in the solid form. Advantageously, the rodenticidal bait according to the invention can be in the form of pellets, granules, a block or a paste liable to be eaten by the target rodent pests or a solid material liable to be gnawed by the target rodent pests. Advantageously, the solid rodenticidal bait according to the invention can be in the form of a rigid block, a semi-rigid block or a gel.

Advantageously and according to the invention, the rodenticidal bait can be in the form of a powder. In particular, such a rodenticidal bait in the form of a powder is suitable for being able to contaminate the fur of the target rodent pest(s) and for being able to be ingested by this(them) during its(their) grooming.

Advantageously and according to the invention, the rodenticidal bait can also be in the liquid form. The rodenticidal bait is then a drink.

Advantageously and according to the invention, the rodenticidal bait comprises at least one colouring agent. Such a colouring agent enables in particular said bait to be given a colour easily detectable and identifiable by a user of said rodenticidal bait.

Advantageously and according to the invention, the rodenticidal bait comprises at least one preservative capable of ensuring it is preserved during its storage.

Advantageously and according to the invention, the rodenticidal bait comprises at least one bittering agent—in particular an amount of denatonium benzoate.

Advantageously, in a variant according to the invention, the rodenticidal bait comprises exclusively difenacoum as the rodenticidal substance. In particular, the rodenticidal bait according to the invention is free from any other anticoagulant substance for rodenticidal use.

However, in another variant according to the invention, the rodenticidal bait can comprise another rodenticidal substance other than difenacoum and/or any other pesticidal substance, such as an insecticidal and/or acaricidal substance.

Advantageously and according to the invention, the rodenticidal bait comprises a mass proportion of trans-difenacoum of between 1 ppm and 30 ppm—in particular between 5 ppm and 25 ppm, preferably between 5 ppm and 15 ppm. The rodenticidal bait according to the invention is thus a rodenticidal bait having a low dose of trans-difenacoum as the substance which inhibits vitamin K epoxide reductase complex subunit 1 (VKORC1). The proportion (in ppm) of trans-difenacoum in the bait is expressed by the amount—in particular by mass—of trans-difenacoum based on the amount—in particular a mass—of bait.

Advantageously and according to the invention, if the target rodent pests are chosen from the group formed by omnivorous rodent mammals of the Muridae family the proportion of trans-difenacoum in the rodenticidal bait is a proportion by mass of between 4 ppm and 12 ppm.

Advantageously and according to the invention, the difenacoum is in a majority in the form of trans-difenacoum. Advantageously, trans-difenacoum is in a majority in the difenacoum. The expression according to which trans-difenacoum is in a majority in the difenacoum indicates that the amount (by mass, molar or by volume) of trans-difenacoum is in a majority—greater than 50%—in the total difenacoum present in the bait (in all its configurational stereoisomeric forms) according to the invention.

Advantageously and according to the invention, the rodenticidal bait comprises trans-difenacoum in a majority in the difenacoum, the trans-difenacoum being the configurational stereoisomer of difenacoum—named homostereoisomer of difenacoum—in which the two carbon atoms 1 and 3 of the 1,2,3,4-tetrahydronaphthalane grouping have the same absolute configuration. The bait comprises an amount of trans-difenacoum in a majority based on the total amount of difenacoum. The bait comprises trans-difenacoum in a majority based on all of the configurational stereoisomers—trans-difenacoum and cis-difenacoum—of the difenacoum. The bait comprises difenacoum in a majority in the form of trans-difenacoum.

In a bait according to the invention:
the amount of trans-difenacoum relative to the sum of the amounts of each of the configurational stereoisomers (i) of difenacoum (trans-difenacoum and cis-difenacoum) is greater than 0.5 (50%):

$$\frac{\text{Amount of trans-difenacoum}}{\sum_i [\text{Amount of stereoisomer}(i) \text{ of difenacoum}]} > 0.5 (50\%)$$

the concentration of trans-difenacoum relative to the sum of the concentrations of each of the configurational stereoisomers (i) of difenacoum (trans-difenacoum and cis-difenacoum) is greater than 0.5 (50%):

$$\frac{[\text{trans-difenacoum}]}{\sum_i [\text{stereoisomer}(i) \text{ of difenacoum}]} > 0.5 (50\%)$$

the proportion ($p_{trans\text{-}difenacoum}$) of trans-difenacoum is greater than the proportion ($p_{cis\text{-}difenacoum}$) of cis-difenacoum. In a bait according to the invention, the proportion of trans-difenacoum is more than 50%, based on the total difenacoum.

The inventors have found that trans-difenacoum and cis-difenacoum do not have the same hepatic persistence in the target rodent pests and that trans-difenacoum is in fact the configurational stereoisomer of difenacoum which has a lower hepatic persistence in the target rodents, in particular in the target rodent pests. They have found that when it is ingested by a target rodent pest, the trans-difenacoum of a bait disappears from the liver of the target rodent pest which has eaten such a bait according to the invention more quickly than cis-difenacoum. The dead or alive target rodent pest which has ingested said bait is less dangerous to non-rodent mammals and birds which eat the target rodent pest and in particular to predators (non-rodent mammals and birds) which preferentially eat the internal organs of their prey and in particular their liver.

The inventors have also found that such a bait according to the invention comprising in a majority trans-difenacoum of lesser hepatic persistence in the target rodent pests in fact allows effective combating of target rodent pests.

Advantageously and according to the invention, trans-difenacoum is present in the bait in an amount greater than 50%—in particular greater than 70%, preferably of between 80% and 100%, more preferably between 90% and 99%—based on the total amount of difenacoum. Advantageously, trans-difenacoum is present in the bait in an amount of between 92% and 98%, based on the total amount of difenacoum. However, there is nothing to prevent trans-difenacoum from being present in the bait in an amount essentially of the order of 100%, based on the total amount of difenacoum.

Advantageously, the bait can comprise the other configurational stereoisomer of difenacoum, named cis-difenacoum, in which carbon atoms 1 and 3 of the 1,2,3,4-tetrahydronaphthalene grouping of difenacoum have different absolute configurations. Advantageously, said cis-difenacoum is present in the bait in an amount of less than 50%—in particular less than 30%, preferably between 0% and 20%, in particular less than 10%, more preferably of the order of 5%—based on the total amount of difenacoum. Advantageously, the bait can be free from cis-difenacoum. Advantageously, the cis-difenacoum is present in the bait in a proportion that is non-lethal to the target rodents. Advantageously, the cis-difenacoum and the trans-difenacoum are present in the bait in a cis-difenacoum/trans-difenacoum mole ratio that is within the range [0:1/19] (0 excluded, 1/19 included).

The invention also relates to a method of selective combating of a population of target rodent pests by scattering a bait liable to be ingested by the target rodent pests and comprising trans-difenacoum, characterised in that the bait comprises an excipient which is edible for the target rodent pests and a proportion of trans-difenacoum in the bait which is greater than a minimum proportion which is lethal to adult females of the target rodents and less than a minimum proportion which is lethal to adult males of the target rodents, said minimum proportion which is lethal to adult females being less than the minimum proportion which is lethal to adult males, and in that these baits are scattered in an amount sufficient to be lethal to adult females of the target rodents.

The invention thus relates to a method of selective combating of a population of target rodent pests by scattering a bait liable to be ingested by the target rodent pests, said bait comprising:
  difenacoum in the form of trans-difenacoum having the formula 3-(biphenyl-4-yl)-1-(4-hydroxycoumarin-3-yl)-1,2,3,4-tetrahydronaphthalene, in which carbon atoms 1 and 3 of the 1,2,3,4-tetrahydronaphthalene grouping of trans-difenacoum have the same absolute configuration, and
  an excipient which is edible for target rodent pests;
characterised in that the bait comprises a proportion of trans-difenacoum in the bait which is greater than a minimum proportion which is lethal to adult females of the target rodents and less than a minimum proportion which is lethal to adult males of the target rodents, said minimum proportion which is lethal to adult females being less than the minimum proportion which is lethal to adult males, and in that these baits are scattered in an amount sufficient to be lethal to adult females of the target rodents.

The invention thus relates to such a method of selective combating of a population of target rodent pests by scattering a bait liable to be ingested by the target rodent pests, in which the bait comprises:
  difenacoum in the form of a configurational stereoisomer of difenacoum, called trans-difenacoum, said trans-difenacoum having the formula 3-(biphenyl-4-yl)-1-(4-hydroxycoumarin-3-yl)-1,2,3,4-tetrahydronaphthalene, carbon atoms 1 and 3 of the 1,2,3,4-tetrahydronaphthalene grouping of trans-difenacoum having the same absolute configuration, and
  an excipient which is edible for the target rodent pests.

In a method of selective combating of a population of target rodent pests according to the invention, an amount of rodenticidal bait liable to be ingested by the target rodent pests is made available to the target rodent pests, said amount of bait being sufficient to kill females of the target rodent pests, said bait comprising trans-difenacoum in a proportion which is greater than a minimum proportion which is lethal to adult females of the target rodents and less than a minimum proportion which is lethal to adult males of the target rodents.

In a method of selective combating according to the invention the proportion of trans-difenacoum in the bait and the amount of bait scattered are adjusted such that—in particular following eating during several days of at least some of the bait by the females—the females of the population of rodents are killed, without the intention being to kill the males of the rodent population.

In a method of selective combating according to the invention, an amount of baits—in particular an amount of baits having lower doses of trans-difenacoum than the known baits comprising difenacoum—and which are thus less toxic to the environment and to non-target animals liable to eat said bait only occasionally and accidentally is scattered. In one method according to the invention, such bait which is less toxic to non-target animals (for example predators of the target rodents) liable to eat the target rodents—dead or alive—which have ingested an amount of said bait is scattered. However, the method according to the invention remains effective for combating the development of populations of target rodent pests by aiming selectively at the females of the target rodent pests.

The inventors have found, totally surprisingly and unforeseeably, that the hepatic persistence of difenacoum in the adult females of target rodent pests which have eaten such a bait comprising trans-difenacoum—in particular a bait having a low dose of trans-difenacoum—is greater than the hepatic persistence of difenacoum in the adult males. The adult females of target rodent pests have an increased coagulation time compared with the coagulation time of the adult males and are more sensitive than the adult males to baits comprising trans-difenacoum—in particular to baits having low doses of trans-difenacoum. They have also found that it is possible to control the population of target rodent pests without using doses of difenacoum which are toxic to the environment and non-target animals by selectively aiming at the adult females, which limits the number of litters of target rodent pests.

A method of selective combating according to the invention:
  allows preferential poisoning—in particular selective poisoning—of the adult females of target rodent pests;
  allows limiting of the amount of difenacoum in the body—in particular in the liver—of the poisoned target rodent pests (alive or dead);
  allows limiting of the amount of difenacoum liable to be ingested by a human being or a non-target animal when the bait is accidentally eaten,
  allows limiting of the amount of difenacoum liable to be ingested by a predator—in particular by a bird in general and in particular by a bird of prey—or by a carrion eater which has eaten a corpse of a target rodent pest poisoned beforehand by such baits.

A method of selective combating according to the invention thus allows the female target rodent pests to be aimed at selectively, limiting the increase in the population of target rodent pests while limiting the risks of poisoning of a human being or non-target animals or predators and/or carrion eaters of the target rodent pests.

Advantageously and according to the invention, the proportion of trans-difenacoum in the bait and the amount of bait scattered are adjusted to achieve:
  in the adult females of the target rodent pests, an amount of trans-difenacoum which is lethal to said adult females, and
  in the adult males of the target rodent pests, an amount of trans-difenacoum which is non-lethal to said adult males.

In a first variant of a method of selective combating according to the invention, the proportion of trans-difenacoum in the bait is chosen in combination with the amount of bait scattered such that adult females of the target rodents eat during a single period of 24 consecutive hours an amount of bait that is sufficient to be lethal to said adult females of the target rodents consuming said bait.

Advantageously in this variant, an amount of bait is scattered that is sufficient to be lethal to the females of target rodent pests eating said bait during a single period of 24 consecutive hours, without the intention being to kill the males of the population of rodents. Advantageously, in this variant of a method of selective combating of target rodent pests according to the invention, a bait which is fatal in a single dose, or "one-shot" bait, is scattered.

Advantageously and according to this variant of the invention, a single eating of the bait by females of target rodent pests is sufficient to cause the death of females of target rodent pests.

In a second variant of a method of selective combating according to the invention, the proportion of trans-difenacoum in the bait is chosen in combination with the amount of bait scattered such that the adult females of target rodent pests eat an amount of difenacoum that is:
- non-lethal for the adult females of target rodent pests which eat said bait during a period of 24 consecutive hours, and
- sufficient to be lethal to the adult females of target rodent pests which eat said bait during several consecutive periods of 24 hours, said periods being successive.

In this second variant of a method of selective combating according to the invention, an amount of bait is scattered which is sufficient to be lethal to the females of target rodent pests ingesting said baits during at least two consecutive days but which is insufficient to cause the death of target rodent pests or of non-target animals by accidental ingestion of a single ration of said baits.

In this second variant of a method of selective combating according to the invention, the proportion of trans-difenacoum in the bait is chosen in order to be able to achieve in the females of the target rodent pests which have eaten such a bait during at least two consecutive days a minimum amount of trans-difenacoum which is lethal to said adult females, and to achieve in the adult males of the target rodent pests which have eaten such a bait during at least two consecutive days an amount of trans-difenacoum which is non-lethal to said adult males.

Advantageously and according to the invention, the proportion of trans-difenacoum in the bait and the amount of bait scattered are chosen in order to allow the adult female(s) to ingest a daily dose by mass of trans-difenacoum of between 0.2 and 10 mg—preferably between 0.2 and 2 mg—of trans-difenacoum per kilogram of adult female.

Advantageously and according to the invention, the amount of trans-difenacoum which is lethal to the adult female(s) is achieved after ingestion of a plurality of daily doses of said bait by the adult female(s). In a method according to the invention, the females of the target rodent pests are eliminated progressively after several successive ingestions of daily doses of bait having a low dose of trans-difenacoum.

Advantageously and according to the invention, the proportion of trans-difenacoum in the bait and the amount of bait scattered are chosen in order to be able to achieve in the liver of the adult females on the day (D+4) following the third day (D+3) of a period of three consecutive days (D+1, D+2 and D+3), each day of said period comprising at least one ingestion of bait, an amount of trans-difenacoum of less than or equal to 10 µg—in particular between 3 µg and 8 µg—of trans-difenacoum per gram of liver of said adult females.

Advantageously and according to the invention, the proportion of trans-difenacoum in the bait and the amount of bait scattered are chosen in order to be able to achieve in the liver of the adult females, on the day following a third ingestion of three successive daily ingestions, an amount of trans-difenacoum less than or equal to 10 µg of trans-difenacoum per gram of liver of said adult females.

The period of three consecutive days during which a target rodent pest ingests the bait can start by counting from a first ingestion of bait by a target rodent pest. It can also start by counting from the start of scattering of the bait.

Advantageously and according to the invention, the proportion of trans-difenacoum in the bait is adjusted in order to be able to achieve in the liver of the adult males on the day (D+4) following the third day (D+3) of a period of three consecutive days (D+1, D+2 and D+3), each day of said period comprising at least one ingestion of bait, an amount of trans-difenacoum less than or equal to 3 µg of trans-difenacoum per gram of liver of the adult males.

Advantageously and according to the invention, the three successive daily ingestions of bait by the adult females in an amount of from 0.2 to 10 mg of trans-difenacoum per ingestion and per kilogram of adult female—preferably from 0.2 to 2 mg—are adjusted in order to be lethal to the adult females in 4 to 8 days counting from the first of the three ingestions.

Advantageously and according to the invention, in a method of selective combating of a population of target rodent pests, a bait according to the invention is used.

A first independent aspect of a bait and a method of selective combating of a population of target rodent pests according to the invention relates to a method of combating a population of target rodent pests by scattering baits liable to be ingested by the target rodent pests and comprising difenacoum, in which trans-difenacoum, which is the configurational stereoisomer of difenacoum which is less persistent in the liver of the target rodent pests, is in a majority in the difenacoum.

Advantageously, according to this first aspect, an amount of rodenticidal bait, that is to say a bait comprising a proportion in a majority of trans-difenacoum, said amount of bait being sufficient to be rodenticidal, is scattered. An amount of bait comprising in a majority trans-difenacoum having in the target rodent pests a hepatic persistence lower than that of a bait comprising in a majority cis-difenacoum, but maintaining a rodenticidal efficacy, is thus scattered. The method according to this first aspect thus allows limiting of the secondary poisoning of non-rodent mammals and birds liable to feed on poisoned rodents which are dead or alive but contain a rodenticidal amount of difenacoum. The method according to this first aspect also allows limiting of such a secondary poisoning of non-rodent mammals and birds liable to preferentially eat the internal organs—in particular the liver—of said poisoned rodents which are dead or alive.

Advantageously, according to this first aspect, it is possible for the bait to comprise cis-difenacoum, but in a proportion that is non-lethal to the target rodents.

Advantageously, according to this first aspect, the mole ratio of cis-difenacoum and of trans-difenacoum in the bait is within the range [0; 1/19] (0 excluded, 1/19 included).

A second independent aspect of a bait and of a method of selective combating of a population of target rodent pests according to the invention relates to a method of combating target rodent pests in which:
- a bait comprising difenacoum is chosen, and
- an amount of this bait is scattered in combination with a proportion of difenacoum in the bait such that target rodent pests eat an amount of difenacoum which is:
  - non-lethal to the target rodent pests which eat said bait during a period of 24 consecutive hours, and
  - sufficient to be lethal to the target rodent pests which eat said bait during several periods of 24 consecutive hours, said periods being successive.

This second aspect thus relates in particular to a method of combating target rodent pests in which an amount of bait which is lethal to target rodent pests which persistently eat this bait and non-lethal to the non-target rodents or animals which accidentally eat this bait is scattered. This is thus referred to as a "multi-dose" or "multi-feeding" method of combating target rodent pests. In a method according to this second aspect, eating of the bait by a target rodent pest for a duration of 24 hours is insufficient to cause the death of said rodent, whereas repeated eating of baits during at least two consecutive days allows the death of the target rodent pest to be caused. In particular, according to this second other aspect, a single eating of baits is insufficient to cause the death of a target rodent pest, whereas repeated eating of baits for at least two consecutive days allows the death of the target rodent pest to be caused.

Advantageously, according to this second aspect, difenacoum is in a mass proportion of less than 200 ppm in the bait, that is to say less than 200 mg of difenacoum per kilogram of bait. Advantageously, the mass proportion of difenacoum is between 1 ppm and 30 ppm. It may particularly be between 10 ppm and 100 ppm (10 mg to 100 mg of difenacoum per kilogram of bait), especially between 10 ppm and 50 ppm (10 mg to 50 mg of difenacoum per kilogram of bait). Advantageously, the mass proportion of difenacoum is between 5 ppm and 25 ppm, preferably between 5 ppm and 15 ppm, more preferentially about 15 ppm (15 mg of difenacoum per kg of bait). The mass proportion of difenacoum in the bait represents the mass of difenacoum based on the mass of the bait comprising difenacoum.

The invention also relates to a rodenticidal bait, a method of combating and a method of selective combating of target rodent pests, characterised in combination by all or some of the characteristics mentioned above or below.

Other objects, characteristics and advantages of the invention will emerge from reading the following description and the examples given purely as non-limiting and which refer to the attached figures, in which.

Figure 1:
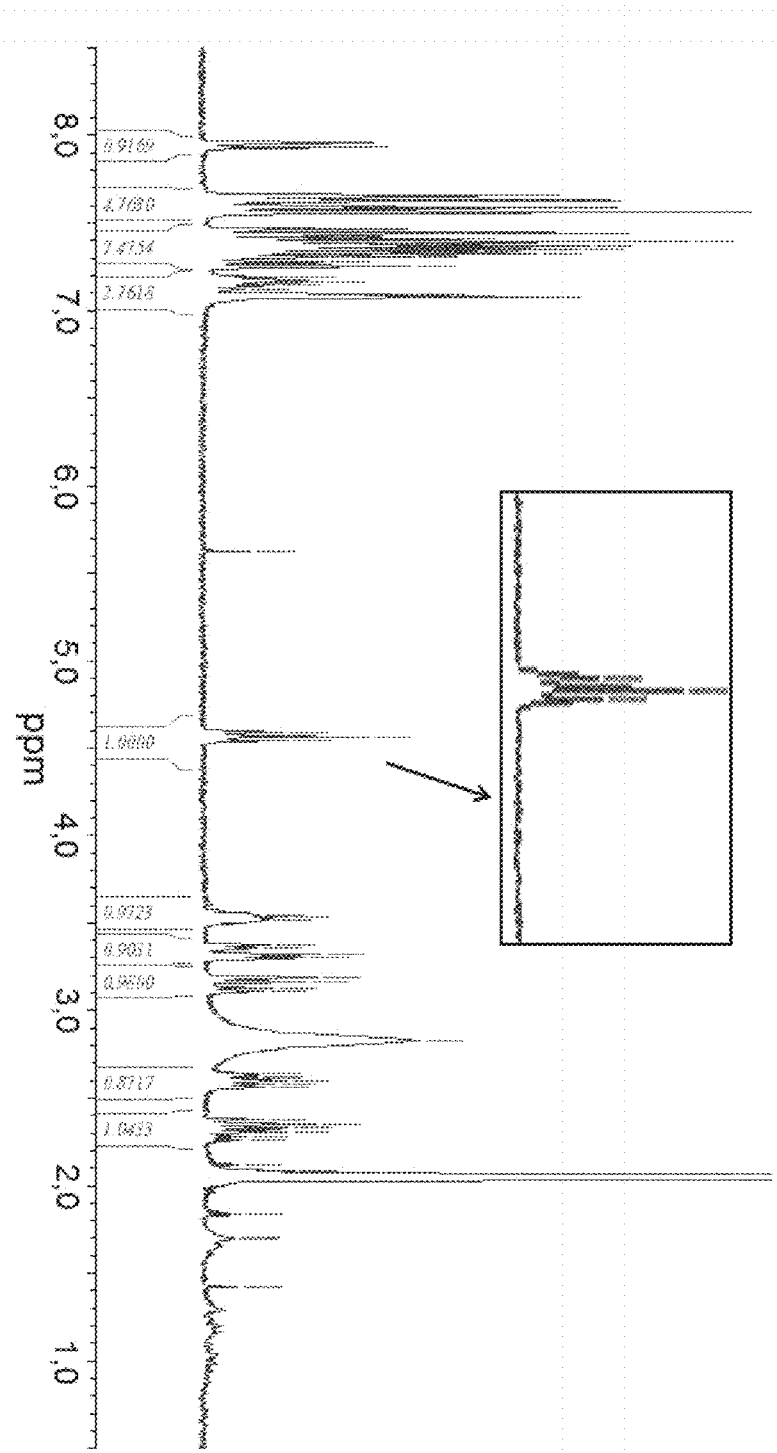
FIG. 1 is a proton NMR spectrum of trans-difenacoum.

A rodenticidal bait according to the invention comprises trans-difenacoum as the rodenticidal agent and at least one attractant substance for target rodent pests, said attractant substance being capable of stimulating the appetite of species of target rodent pests and the ingestion of said bait by the target rodent pests.

trans-Difenacoum is obtained by any method allowing the separation of the cis/trans configurational stereoisomers of difenacoum. For example, the document EP 0 175 466 discloses a method for the separation of the trans and cis configurational stereoisomers of difenacoum by selective precipitation of the cis configurational stereoisomer from a solution of the configurational stereoisomers in an alcohol such as ethanol.

It is also possible to separate the trans-difenacoum and cis-difenacoum configurational stereoisomers by chromatography, for example by high performance liquid chromatography (HPLC), and to form a mixture enriched in trans-difenacoum or a composition of trans-difenacoum essentially free from cis-difenacoum. Such an enrichment is carried out by HPLC, for example on a C8 (250 mm×10 mm) column kept at the temperature of 30° C. The mobile phase is formed from 80% acetonitrile and 20% acid water. The flow rate of the mobile phase is kept at 2 ml/min. The trans-difenacoum and the cis-difenacoum are detected by spectrophotometric analysis at the wavelength of 258 nm.

In particular, such a separation of the trans-difenacoum and cis-difenacoum configurational stereoisomers is described, for example, in the publication "Kelly M. J. et al., (1993), *Journal of Chromatography,* 620, 105-112. Simple and rapid method for the determination of the diastereoisomers of difenacoum in blood and liver using high performance liquid chromatography with fluorescence detection". This document also reports that the cis and trans configurational stereoisomers of difenacoum differ in proton NMR (Brüker AC 300 spectrometer at 300.13 MHz in $CDCl_3$), the signal corresponding to the proton of carbon atom 1 of the 1,2,3,4-tetrahydronaphathalene grouping of trans-difenacoum being a triplet centred at 4.76 ppm and having a coupling constant of 4.20 Hz and the signal of the proton of carbon atom 1 of the 1,2,3,4-tetrahydronaphathalene grouping of cis-difenacoum being a quartet centred at 4.9 ppm and having coupling constants of 11.9 and 6 Hz with the protons of carbon atom 2 of the 1,2,3,4-tetrahydronaphathalene grouping.

It is also possible to carry out an enrichment of trans-difenacoum by HPLC chromatography on an INERTSIL® ODS2 reverse phase column of 150 mm length and 4.6 mm internal diameter. The reverse stationary phase has a particle size of 5 µm, a porosity of 80 Å and a specific surface area of 500 $m^2/g$. The mobile phase is made up of a mixture of acetonitrile (62%), isopropanol (3%) and ammonium acetate (35%) adjusted to pH 4 with acetic acid. The flow rate of the mobile phase is 1.5 ml/min and the detection is carried out by spectrophotometry at 260 nm. A "trans" configurational stereoisomer of which the retention time is of the order of 5.74 min and another "cis" configurational stereoisomer of which the retention time is of the order of 4.87 min are detected and collected.

The separation of the "trans" and "cis" configurational stereoisomers of difenacoum can also be carried out by ultra-performance liquid chromatography (UPLC, Waters) on an Acquity Waters chain comprising an Acquity UPLC BEH C18 column of 1.7 µm particle size and dimensions of 2.1×50 mm at 35° C. The mobile phase is formed by a gradient of an aqueous solution of trifluoroacetic acid (TFA, 0.1%) and a solution of TFA, 0.1% in acetonitrile. The flow rate of the mobile phase is 0.6 ml/min. The retention time of the configurational stereoisomer retained the most ("trans") is 8.2 min and that of the configurational stereoisomer retained the least ("cis") is of the order of 7.3 min.

The separation of the "trans" and "cis" configurational stereoisomers of difenacoum can also be carried out by high pressure liquid chromatography (HPLC) on an XBridge C18 column (dimensions of 4.6×150 mm and particle size of 5 µm) and with a mobile phase formed by 45% of an aqueous 0.1% solution of TFA and 55% of a solution of TFA at 0.1% in acetonitrile. The flow rate of the mobile phase is 1.2 ml/min. The retention time of the configurational stereoisomer retained the most ("trans") is 23.7 min and that of the configurational stereoisomer retained the least ("cis") is of the order of 21.0 min.

Figure 2:
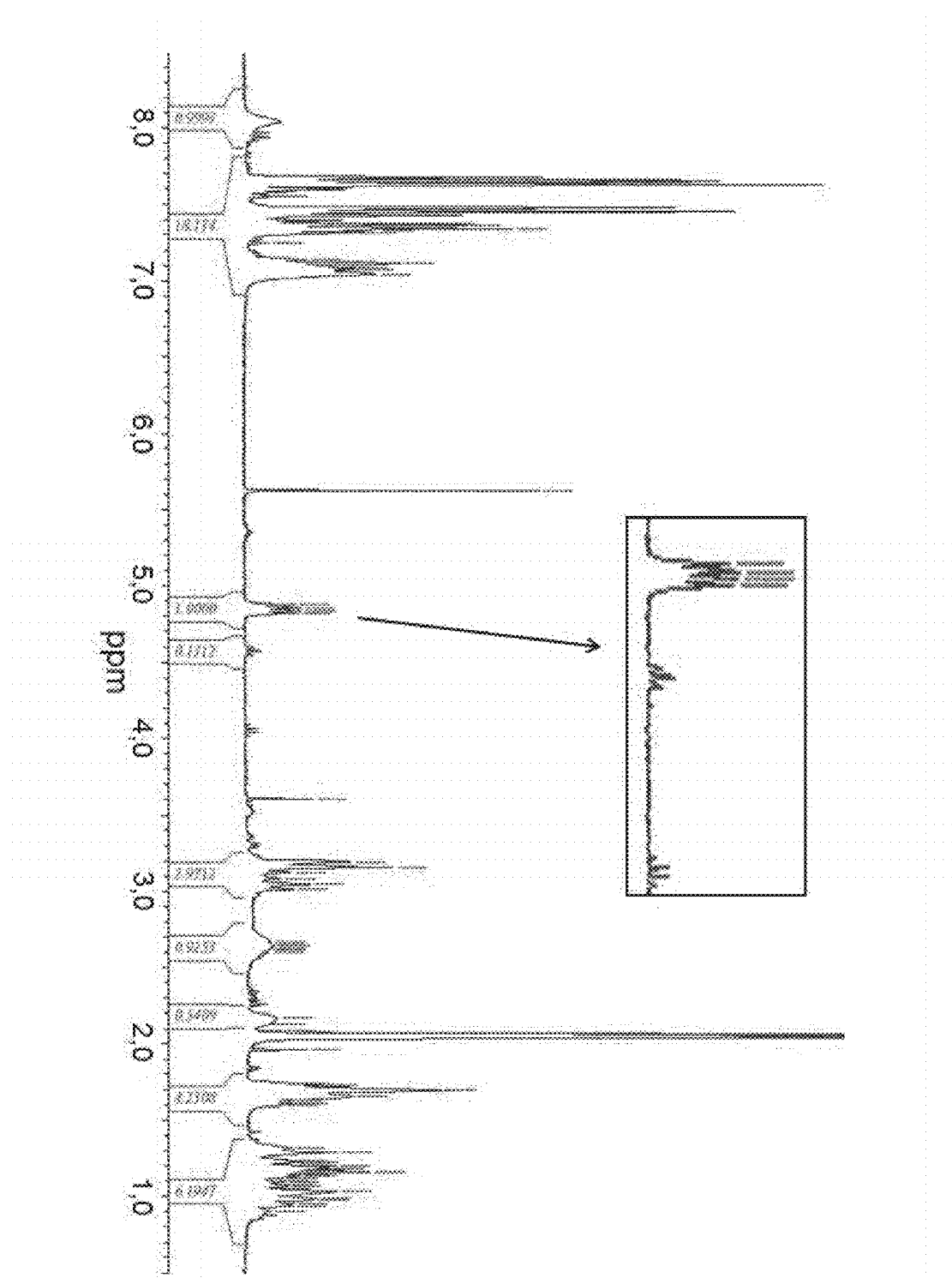
FIG. 2 is a proton NMR spectrum of cis-difenacoum.

The proton NMR spectrum of the "trans" configurational stereoisomer of difenacoum is shown in FIG. 1 and the proton NMR spectrum of the "cis" configurational stereoisomer of difenacoum is shown in FIG. 2. The proton NMR spectrum of trans-difenacoum has a triplet (4.5399 ppm, 4.5644 ppm and 4.5876 ppm) characteristic of the proton carried by carbon atom 1 of the 1,2,3,4-tetrahydronaphathalene grouping. By comparison, the proton NMR spectrum of cis-difenacoum has a quartet (4.8180 ppm, 4.8374 ppm, 4.8550 ppm and 4.8721 ppm) characteristic of the proton carried by carbon atom 1 of the 1,2,3,4-tetrahydronaphathalene grouping.

Hepatic Persistence Compared for the "Trans" and "Cis" Configurational Stereoisomers of Difenacoum in the Rat On D0 per os tube feeding is performed on male laboratory rats (Sprague Dawley rats, Charles River, Saint germain sur l' Arbresle, France) aged 8 weeks and with a body mass of the order of 200 g with a mixture comprising 56% of trans-difenacoum and 44% of cis-difenacoum in an amount of 5.2 mg of difenacoum per kilogram of rat. The rats are kept alive by daily subcutaneous injection of a solution of vitamin K in an amount of 1 U per rat. On D+1, D+3, D+5, D+7, D+10, D+14 and D+21, 4 rats are anaesthetised with isoflurane and then sacrificed, and the livers are removed and frozen until analysed. The mean hepatic contents of trans-difenacoum and cis-difenacoum are analysed by HPLC and are given in Table 1 below.

TABLE 1

| Hepatic content, µg/g | D + 1 | D + 3 | D + 5 | D + 10 | D + 21 |
|---|---|---|---|---|---|
| trans | 4.22 | 1.05 | 0.25 | 0.1 | 0.17 |
| cis | 16.82 | 8.28 | 4.86 | 1.85 | 1.41 |

From D+1 the mean content of trans-difenacoum in the liver of rats is lower than the mean content of cis-difenacoum in the livers of rats tube-fed with essentially the same amount of each configurational stereoisomer of difenacoum. trans-Difenacoum has a hepatic persistence significantly lower than that of cis-difenacoum.

An amount of trans-difenacoum is dispersed in an amount of an attractant and nutritive substance for target rodent pests by any method known per se to the person skilled in the art. The amounts of trans-difenacoum and attractant substance are chosen such as to form a rodenticidal bait according to the invention comprising trans-difenacoum in a proportion greater than the minimum proportion which is lethal in less than 10 days to the adult females of the target rodent pests and non-lethal to the adult males of the target rodent pests.

Such a proportion of trans-difenacoum in the rodenticidal bait is adjusted so that female target rodent pests eating the rodenticidal bait, the attractant substance and the trans-difenacoum, ingest an amount of trans-difenacoum which is sufficient to obtain the rodenticidal effect and to control the population of target rodent pests.

1) Comparison of the Rodenticidal Efficacy of Trans-Difenacoum and Cis-Difenacoum in the Male Rat and the Female Rat.

The comparative study of the rodenticidal efficacy of purified trans-difenacoum and purified cis-difenacoum is carried out by administration by means of a stomach tube (per os):
- of a solution of cis-difenacoum to a first group of four "Sprague Dawley" male rats weighing between 180 and 220 g, and
- of a solution of trans-difenacoum to a second group of four "Sprague Dawley" male rats weighing between 180 and 220 g.

These solutions of cis-difenacoum and trans-difenacoum are obtained by weighing cis-difenacoum or trans-difenacoum and dilution in a mixture formed from 95% vegetable oil and 5% DMSO.

The doses of cis-difenacoum and trans-difenacoum used are 2.6 mg of cis-difenacoum or trans-difenacoum per kilogram of rat. The dose of 2.6 mg of cis-difenacoum and trans-difenacoum per kilogram of rat corresponds to 4 times the median lethal dose ($LD_{50}$) of difenacoum for rats. The dose of 5.2 mg of cis-difenacoum or trans-difenacoum per kilogram of rat corresponds to 8 times the median lethal dose ($LD_{50}$) of difenacoum for rats.

3 ml blood samples are taken from the rats anaesthetised with isoflurane in sample tubes containing citrate (3.2%). The tubes are centrifuged at 2,000 g for 10 minutes and the plasma fraction is collected.

The coagulation time (Quick time) of the plasma is analysed by means of the "Neoplastine CI Determination of Prothrombin Time" kit (Diagnostica Stago, Asnière, France) by measurement on a Thrombotimer option 2 plus (Behnk Electronik, Norderstedt, Germany).

The normal value for the coagulation time of untreated rats is 10 to 20 seconds.

The administration ($D_0$) per os of cis-difenacoum in an amount of 2.6 mg of cis-difenacoum per kilogram of rat or of trans-difenacoum in this same dosage of 2.6 mg/kg of rat causes a significant increase in the coagulation time of the rats at 1 day after the administration ($D_{+1}$).

The coagulation time ($D_{+1}$) of the blood of rats treated with a dosage of 2.6 mg of cis-difenacoum or trans-difenacoum per kilogram of rat is 62 seconds. In contrast, the administration per os of trans-difenacoum in this same dosage (2.6 mg/kg) or in double the dosage (5.2 mg/kg) certainly causes an increase in the coagulation time (62 s and 84 s) on $D_{+1}$, but leads to a value of the Quick time on $D_{+3}$ which is low (10 to 20 s) and of the order of size of the Quick time of an untreated control. No indication was therefore given to the inventors to choose a rodenticidal bait comprising trans-difenacoum in a majority.

In addition, the value of the inhibition constant ($Ki_{cis}$=60 nM) of the recombinant enzyme rVKORC1 by cis-difenacoum is similar to the value of the inhibition constant of rVKORC1 by trans-difenacoum ($Ki_{trans}$=30 nM).

2) Hepatic Persistence of Cis-Difenacoum and Trans-Difenacoum in the Male Rat.

Figure 3:
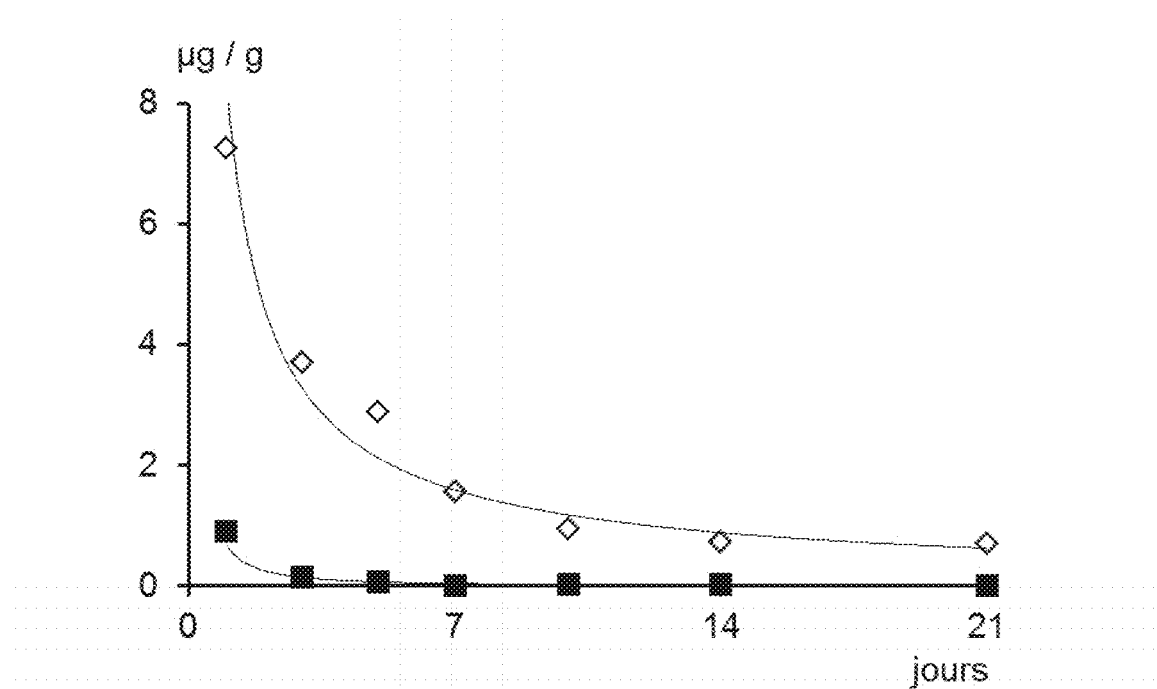
FIG. 3 is a comparative graphical representation of the hepatic persistence of trans-difenacoum and of cis-difenacoum in the rat.

On $D_0$ a control composition of the prior art comprising a molar proportion of cis-difenacoum of 56% and a molar proportion of trans-difenacoum of 44% is administered per os to seven groups of four male laboratory rats (Sprague Dawley rats, Charles River, Saint germain sur l'Arbresle, France) weighing between 180 and 220 g in an amount of 5.2 mg of difenacoum per kilogram of rat. On $D_{+1}$, $D_{+3}$, $D_{+5}$, $D_{+7}$, $D_{+10}$, $D_{+14}$ and $D_{+21}$, 4 rats are sacrificed. The livers are removed and weighed. A liquid/solid extraction of difenacoum with acetone is performed. The difenacoum is analysed by HPLC on a C8 (250 mm×10 mm) column kept at 30° C. with a mobile phase formed from 80% acetonitrile and 20% acid water. The flow rate of the mobile phase is kept at 2 ml/min and the trans-difenacoum and cis-difenacoum are detected by spectrophotometric analysis at the wavelength of 258 nm. The trans-difenacoum and cis-difenacoum are quantified by calibration with known amounts of trans-difenacoum and cis-difenacoum. The results are given in FIG. 3, in which the hepatic persistence of trans-difenacoum is represented by solid squares (■) and the hepatic persistence of cis-difenacoum is represented by open diamonds (◇). Whereas the molar proportion of trans-difenacoum administered to the rats is 46%, the hepatic concentration (expressed in μg of difenacoum per g of liver) of trans-difenacoum at $D_{+1}$ is only of the order of 1 μg/g, trans-difenacoum being almost undetectable from $D_{+3}$, only the cis-difenacoum remaining (4 μg/g).

3) Hepatic Persistence of Trans-Difenacoum and Cis-Difenacoum in the Male Rat and in the Female Rat.

A study comparable to that described under 2), in which a separation and an assay of trans-difenacoum and cis-difenacoum are carried out on $D_{+1}$, $D_{+3}$, $D_{+5}$, $D_{+7}$, $D_{+10}$, $D_{+14}$ and $D_{+21}$, is conducted on treated male rats and female rats. On $D_{+1}$ the concentration of cis-difenacoum in the liver of the female rats (9.6 μg/g of liver) is essentially equivalent to the concentration of cis-difenacoum in the liver of the male rats (7.3 μg/g of liver). The concentration on $D_{+1}$ of trans-difenacoum in the liver of the female rats (3.3 μg/g of liver) is greater than the concentration of trans-difenacoum in the liver of the male rats (0.9 μg/g of liver). In addition, on $D_{+3}$ the value of the concentration of trans-difenacoum in the liver is greater in the female rats in comparison with the male rats. The kinetics of the hepatic elimination of trans-difenacoum are slower in the female rats than in the male rats, in particular during the first 3 days. For the same dosage, the hepatic concentrations of trans-difenacoum are thus higher in the female at least up to three days after treatment ($D_0$).

4) Administration of Trans-Difenacoum to Male Rats, Multi-Dose Treatment ("Multi-Feeding").

Figure 4:
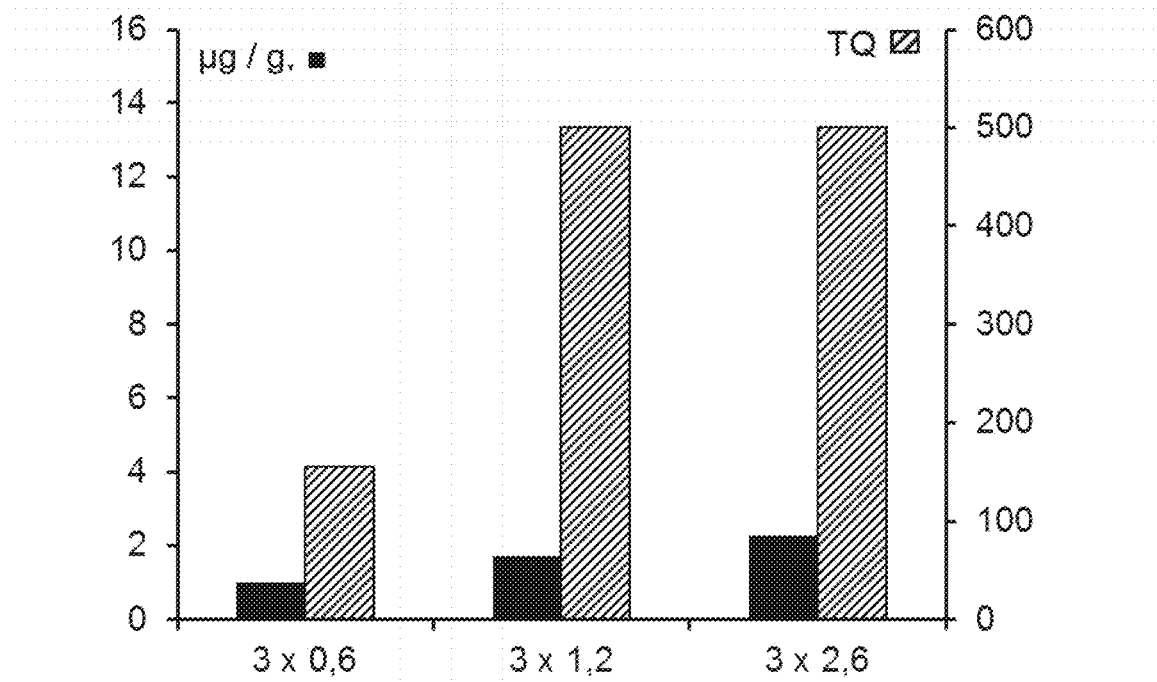
FIG. 4 is a graphical representation of the hepatic persistence (in µg/g of liver) at $D_4$ and the Quick time (QT) of male rats which have received treatment with three doses ($D_1$, $D_2$ and $D_3$) of a solution comprising trans-difenacoum administered in an amount of 0.6; 1.2 or 2.6 mg of difenacoum per kilogram of rat.

Counting from $D_0$ and for three days ($D_0$, $D_{+1}$ and $D_{+2}$), trans-difenacoum in an amount of 0.6 mg/kg, 1.2 mg/kg or 2.6 mg/kg (mg of trans-difenacoum per kilogram of male rat) is administered daily to "Sprague Dawley" male rats weighing between 180 and 220 g. On $D_{+3}$, the coagulation time of these male rats is measured and the concentration of trans-difenacoum in the liver of these male rats (expressed in μg of trans-difenacoum per g of liver) is analysed. The results are given in FIG. 4. The administration for three days ($D_0$, $D_{+1}$ and $D_{+2}$) in an amount of one dose of trans-difenacoum per day to male rats gives rise to a massive increase in the Quick time of these rats on $D_{+3}$ and a moderate value of the hepatic persistence of the order of 2 μg/g of liver.

With a dosage of 1.2 mg/kg or higher (corresponding to a bait dosed with between 12 ppm and 25 ppm of trans-difenacoum), the increase in the Quick time is such that the blood of the male rat is uncoagulable. The probability that this male rat dies of haemorrhage is thus a maximum.

5) Administration of Trans-Difenacoum to Female Rats. Multi-Dose Treatment ("Multi-Feeding").

Figure 5:
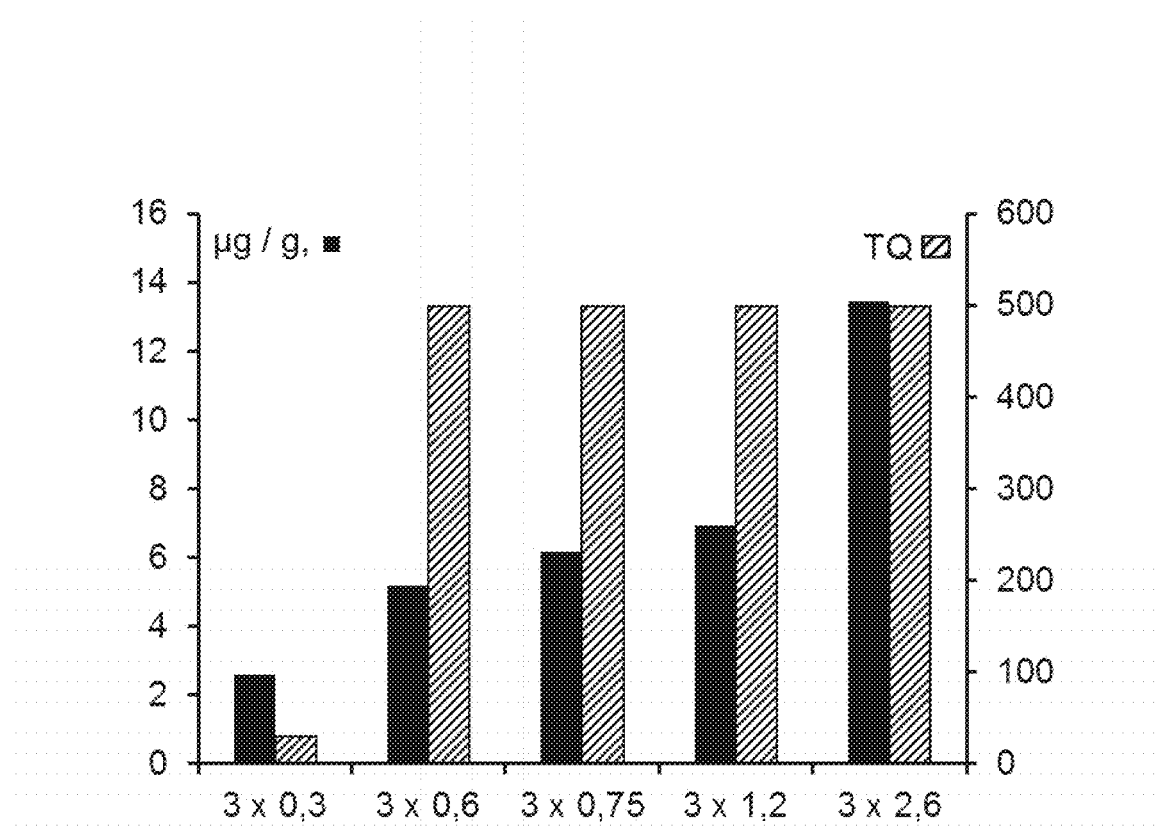
FIG. 5 is a graphical representation of the hepatic persistence (in µg/g of liver) at $D_4$ and the Quick time (QT) of female rats which have received treatment with three doses ($D_1$, $D_2$ and $D_3$) of a solution comprising trans-difenacoum administered in an amount of 0.3; 0.6; 0.75; 1.2 or 2.6 mg of difenacoum per kilogram of rat.

Counting from $D_0$ and for three days ($D_0$, $D_{+1}$ and $D_{+2}$), trans-difenacoum in an amount of 0.3 mg/kg; 0.6 mg/kg; 0.75 mg/kg; 1.2 mg/kg or 2.6 mg/kg (mg of trans-difenacoum per kilogram of female rat) is administered to female "Sprague Dawley" rats in an amount of one dose per day. On $D_{+4}$, the coagulation time of these female rats is measured and the concentration of trans-difenacoum in the liver (expressed in μg of difenacoum per g of liver) of these rats is analysed. The results are given in FIG. 5. The administration for three days ($D_0$, $D_{+1}$ and $D_{+2}$) in an amount of a dose of trans-difenacoum greater than 0.3 mg/kg/day to female rats achieves at $D_{+4}$ a high value of the coagulation time (greater than or equal to 500 seconds) in these female rats and a moderate hepatic persistence of less than 10 μg of trans-difenacoum per gram of liver for a dose of less than 2.6 mg/kg.

With a dosage of 0.6 mg/kg or higher (corresponding to a rodenticidal bait dosed with between 6 ppm and 25 ppm of trans-difenacoum), the increase in the coagulation time is such that the blood of the female rats is uncoagulable. The probability that these female rats die of haemorrhage is thus a maximum.

A rodenticidal bait comprising trans-difenacoum in a majority and a method of combating target rodent pests using such a rodenticidal bait according to the invention allows an anticoagulant effect to be obtained on repeated administration (multi-dose) of trans-difenacoum and very low hepatic concentrations in the male rats with a dosage of 3 times 2.6 mg/kg and in the female rats with a dosage of less than 2.6 mg/kg.

The hepatic concentration of trans-difenacoum is of the order of 2 μg/g of liver of the male rat the day following the last dose of rodenticidal bait. Considering that the mass of a rat liver is of the order of 10 g, the global amount of trans-difenacoum is 20 μg per liver, and considering that the liver contains half the trans-difenacoum ingested by the rodent, a rat corpse would contain about 40 μg of trans-difenacoum. Consequently, the corpses of rats killed by ingestion of a bait according to the invention present a reduced ecotoxicological risk with respect to corpses of rats killed by ingestion of a bait of the prior art.

By way of example, the hepatic concentration of trans-difenacoum of female rats treated with a bait allowing the administration of 2.6 mg of trans-difenacoum per day and per kilogram of rat for 3 days is of the order of 12 μg/g of liver. Since predators of rodents rapidly eliminate trans-difenacoum, a corpse of a female target rodent pest containing such a dose of trans-difenacoum is much less dangerous to the environment than a corpse of a female target rodent pest containing the same amount of the cis-difenacoum configurational stereoisomer.

Thus, the use of trans-difenacoum in a bait in which trans-difenacoum is in a majority is less dangerous to species exposed to the risk of primary intoxication (ingestion of the bait according to the invention by a non-target animal—by a dog, for example). Eating a bait according to the invention containing trans-difenacoum in a majority is liable to present problems to a non-target animal only if said non-target animal can have access to significant amounts of said rodenticidal bait repeatedly over time. The risk is thus reduced considerably with respect to the use of a commercial mixture which is liable to cause a fatal intoxication in the dog in a single dose.

6) Treatment of a Population of Rats with a Bait According to the Invention Comprising 50 ppm of Trans-Difenacoum.

Rodenticidal baits are prepared by dispersing an amount of difenacoum in a paste based on flour and vegetable fat such that the bait contains 50 mg of difenacoum per kilogram of bait (50 ppm of difenacoum).

The following are prepared:
  a rodenticidal bait according to the invention comprising trans-difenacoum in a majority (91% of trans-difenacoum and 9% of cis-difenacoum), and
  by way of comparison baits comprising:
    4% of trans-difenacoum and 96% of cis-difenacoum, and
    38% of trans-difenacoum and 62% of cis-difenacoum.

Rodents (10 Sprague Dawley (SD) rats, 5 males and 5 females) are placed in individual cages. During 4 days (D1, D2, D3 and D4) each rat is supplied with an amount of bait sufficient to satisfy its appetite. At the end of these 4 days food free from bait is provided. The daily consumption of each bait is measured by weighing. On the death of the animal the liver of the dead animal is removed, frozen and stored until the hepatic content of configurational stereoisomers of difenacoum is analysed.

The mean daily consumption of bait by the rats and the time at which the death of the animals occurs and the mortality are given in Table 2 below.

TABLE 2

| trans-Difenacoum/ cis-Difenacoum | Mean mass of bait consumed daily, g/day | Time of death | Mortality, % |
|---|---|---|---|
| 91/9 | 12.9 | D4 to D8 | 90 |
| 38/62 | 12.5 | D4 to D9 | 90 |
| 4/96 | 11.8 | D5 to D9 | 100 |

The bait according to the invention (91/9) is eaten by the rats with the same mean daily amount as the baits (2/98 or 18/82) not enriched in trans-difenacoum. The time at which death occurs in the animals having eaten the bait according to the invention is shorter (D4-D8) than the time at which death occurs in the animals having eaten baits 38/62 (D4 to D9) and 4/96 (D5 to D9).

The results of the hepatic assays of trans-difenacoum and cis-difenacoum are presented in Table 3 below, in which "trans-difenacoum/cis-difenacoum" represents the amount (molar or by mass) of trans-difenacoum relative to the amount (molar or by mass) of cis-difenacoum in the bait made available to the rats and the term "Residue" represents the percentage of difenacoum (trans-difenacoum and cis-difenacoum) detected in the liver of the rats relative to the total mean amount of difenacoum ingested by each rat.

TABLE 3

| trans-Difenacoum/ | Hepatic content, μg/g | | Residue, |
|---|---|---|---|
| cis-Difenacoum | trans-Difenacoum | cis-Difenacoum | % |
| 91/9 | 0.76 | 0.63 | 0.4 |
| 38/62 | 0.15 | 1.54 | 0.59 |
| 4/96 | 0.01 | 2.16 | 0.7 |

The mean content of difenacoum in the liver of the male rats is 8.4 μs (4.3 μs of trans-difenacoum and 4.1 μg of cis-difenacoum), 13.5 μs (1.4 μs of trans-difenacoum and 12.1 μs of cis-difenacoum) and 21.9 μs (0.2 μs of trans-difenacoum and 21.7 μs of cis-difenacoum) per male rat treated, respectively, with the baits (91/9), (38/62) and (4/96). The residues of difenacoum in the liver of the male rats are minimised with the use of the bait according to the invention.

The mean content of difenacoum in the liver of the female rats is 14.9 μs (8.5 μs of trans-difenacoum and 6.4 μg of cis-difenacoum), 16.4 μs (1.1 μg of trans-difenacoum and 15.2 μg of cis-difenacoum) and 10.8 μg (10.7 μg of cis-difenacoum) per female rat treated with, respectively, the baits (91/9), (38/62) and (4/96). The residues of difenacoum in the liver of the female rats are minimised with the use of the bait according to the invention. The residues of difenacoum in the liver of the male rats are also minimised with respect to the residues of difenacoum in the liver of the female rats with the use of the bait (91/9) according to the invention.

A bait (91/9) comprising trans-difenacoum in a majority thus allows limiting of the residues of difenacoum in the liver of rodents and their secondary toxicity to predators of rodents or carrion eaters of corpses of rodents.

7) Treatment of a Population of Rats with a Bait According to the Invention Comprising 15 ppm of Trans-Difenacoum.

Rodenticidal baits are prepared by dispersing an amount of difenacoum in a paste based on flour and vegetable fat such that the bait contains 15 mg of difenacoum per kilogram of bait (15 ppm of difenacoum).

The following are prepared:
a rodenticidal bait according to the invention comprising trans-difenacoum in a majority (essentially 100% of trans-difenacoum), and
by way of comparison a bait comprising 100% of cis-difenacoum.

Rodents (10 Sprague Dawley (SD) rats, 5 males and 5 females) are placed in individual cages and treated as described under 6) above. The mean daily consumption of bait by the rats and the time at which the death of the animals occurs and the mortality are given in Table 4 below.

TABLE 4

| trans-Difenacoum/ cis-Difenacoum | Mean mass of bait consumed daily, g/day | Time of death | Mortality, % |
|---|---|---|---|
| 100/0 | 14.8 | D5 to D8 | 70% |
| 0/100 | 13.8 | D4 to D9 | 100% |

The bait comprising 15 ppm of difenacoum according to the invention (essentially of the order of 100% trans-difenacoum in the difenacoum) is eaten by the rats with the same mean daily amount as the bait (100% cis-difenacoum). The time at which death occurs in the animals having eaten the bait according to the invention is comparable (D5-D8) to the time at which death occurs in the animals having eaten the bait having a low dose of trans-difenacoum (D4 to D9).

A bait according to the invention comprising trans-difenacoum in a majority thus allows limiting of the residues of difenacoum in the liver of rodents and their secondary toxicity to predators of rodents or carrion eaters of corpses of rodents while preserving a rodenticidal efficacy of the order of 70% with a bait having a low dose of 15 ppm.

It goes without saying that the invention may be subject to numerous embodiments and applications. In particular, a rodenticidal bait and a method of combating at least one species of target rodent pests are subject to an infinite number of variants both in the formulation of the bait and in the modes of implementation of the method.

The invention claimed is:

1. Rodenticidal bait comprising:
   difenacoum in a majority in the form of trans-difenacoum having the formula 3-(biphenyl-4-yl)-1-(4-hydroxycoumarin-3-yl)-1,2,3,4-tetrahydronaphthalene, in which carbon atoms 1 and 3 of the 1,2,3,4-tetrahydronaphthalene grouping of trans-difenacoum have the same absolute configuration, and;
   an excipient which is edible for target rodent pests; wherein a proportion of trans-difenacoum in the bait is greater than a minimum proportion of trans-difenacoum which is lethal to adult females of the target rodents and less than a minimum proportion of trans-difenacoum which is lethal to adult males of the target rodents, said minimum proportion which is lethal to adult females being less than the minimum proportion which is lethal to adult males.

2. Bait according to claim 1, wherein the excipient which is edible comprises at least one food selected from the group consisting of cereal grains, ground cereal grains, cereal grain flours, cereal grain flakes, cereal bran, non-cereal grains, ground non-cereal grains, non-cereal grain flours, non-cereal grain flakes, and non-cereal plant bran.

3. Bait according to claim 1, having a proportion by mass of trans-difenacoum of between 1 ppm and 30 ppm.

4. Method of selective combating of a population of target rodent pests by scattering a bait liable to be ingested by the target rodent pests, said bait comprising:
difenacoum in a majority in the form of trans-difenacoum having the formula 3-(biphenyl-4-yl)-1-(4-hydroxy-coumarin-3-yl)-1,2,3,4-tetrahydronaphthalene, in which carbon atoms 1 and 3 of the 1,2,3,4-tetrahydronaphthalene grouping of trans-difenacoum have the same absolute configuration, and
an excipient which is edible for target rodent pests;
wherein a proportion of trans-difenacoum in the bait is greater than a minimum proportion which is lethal to adult females of the target rodents and less than a minimum proportion which is lethal to adult males of the target rodents, said minimum proportion which is lethal to adult females being less than the minimum proportion which is lethal to adult males, and wherein these baits are scattered in an amount sufficient to be lethal to adult females of the target rodents.

5. Method according to claim 4, wherein the proportion of trans-difenacoum in the bait and the amount of bait scattered are adjusted to achieve:
in the adult females of the target rodent pests, an amount of trans-difenacoum which is lethal to said adult females, and
in the adult males of the target rodent pests, an amount of trans-difenacoum which is not lethal to said adult males.

6. Method according to claim 4, wherein the proportion of trans-difenacoum in the bait is chosen in combination with the amount of bait scattered such that adult females of the target rodents eat during a single period of 24 consecutive hours an amount of bait sufficient to be lethal to said adult females of the target rodents which eat said bait.

7. Method according to claim 4, wherein the proportion of trans-difenacoum in the bait is chosen in combination with the amount of bait scattered such that the adult females of target rodent pests eat an amount of difenacoum which is:
non-lethal to the adult females of target rodent pests which eat said bait during a period of 24 consecutive hours, and
sufficient to be lethal to the adult females of target rodent pests which eat said bait during several periods of 24 consecutive hours, said periods being successive.

8. Method according to claim 7, wherein the amount of trans-difenacoum which is lethal to the adult female(s) is achieved after ingestion of a plurality of daily doses of said bait by the adult female(s).

9. Method according to claim 4, wherein the proportion of trans-difenacoum in the bait and the amount of bait scattered are chosen in order to be able to achieve in the liver of the adult females, on the day following the third day of a period of three consecutive days, each day of said period comprising at least one ingestion of bait, an amount of trans-difenacoum of less than or equal to 10 µg of trans-difenacoum per gram of liver of said adult females.

10. Method according to claim 4, wherein the bait is chosen in order to allow preferential poisoning of the adult females of target rodent pests.

11. Bait according to 2, having a proportion by mass of trans-difenacoum of between 1 ppm and 30 ppm.

12. Method according to claim 5, wherein the proportion of trans-difenacoum in the bait is chosen in combination with the amount of bait scattered such that adult females of the target rodents eat during a single period of 24 consecutive hours an amount of bait sufficient to be lethal to said adult females of the target rodents which eat said bait.

13. Method according to claim 5, wherein the proportion of trans-difenacoum in the bait is chosen in combination with the amount of bait scattered such that the adult females of target rodent pests eat an amount of difenacoum which is:
non-lethal to the adult females of target rodent pests which eat said bait during a period of 24 consecutive hours, and
sufficient to be lethal to the adult females of target rodent pests which eat said bait during several periods of 24 consecutive hours, said periods being successive.

14. Method according to claim 5, wherein the proportion of trans-difenacoum in the bait and the amount of bait scattered are chosen in order to be able to achieve in the liver of the adult females, on the day following the third day of a period of three consecutive days, each day of said period comprising at least one ingestion of bait, an amount of trans-difenacoum of less than or equal to 10 µg of trans-difenacoum per gram of liver of said adult females.

15. Method according to claim 6, wherein the proportion of trans-difenacoum in the bait and the amount of bait scattered are chosen in order to be able to achieve in the liver of the adult females, on the day following the third day of a period of three consecutive days, each day of said period comprising at least one ingestion of bait, an amount of trans-difenacoum of less than or equal to 10 µg of trans-difenacoum per gram of liver of said adult females.

16. Method according to claim 7, wherein the proportion of trans-difenacoum in the bait and the amount of bait scattered are chosen in order to be able to achieve in the liver of the adult females, on the day following the third day of a period of three consecutive days, each day of said period comprising at least one ingestion of bait, an amount of trans-difenacoum of less than or equal to 10 µg of trans-difenacoum per gram of liver of said adult females.

17. Method according to claim 8, wherein the proportion of trans-difenacoum in the bait and the amount of bait scattered are chosen in order to be able to achieve in the liver of the adult females, on the day following the third day of a period of three consecutive days, each day of said period comprising at least one ingestion of bait, an amount of trans-difenacoum of less than or equal to 10 µg of trans-difenacoum per gram of liver of said adult females.

* * * * *